United States Patent [19]

Bergomi et al.

[11] 4,144,272

[45] Mar. 13, 1979

[54] METHOD OF PREPARING TETRAALKYL THIURAM DISULFIDES

[75] Inventors: Angelo Bergomi, Akron; James J. Tazuma, Stow, both of Ohio

[73] Assignee: The Goodyear Tire & Rubber Company, Akron, Ohio

[21] Appl. No.: 860,494

[22] Filed: Dec. 14, 1977

Related U.S. Application Data

[63] Continuation of Ser. No. 679,527, Apr. 23, 1976, abandoned, which is a continuation of Ser. No. 493,577, Aug. 1, 1974, abandoned, which is a continuation of Ser. No. 301,692, Oct. 27, 1972, abandoned.

[51] Int. Cl.$^2$ ............................................. C07C 155/10
[52] U.S. Cl. .................................................... 260/567
[58] Field of Search ........................................ 260/567

[56] References Cited

U.S. PATENT DOCUMENTS

| 1,413,172 | 4/1922 | Lorentz | 260/567 |
| 1,782,111 | 11/1930 | Adams | 260/567 |

*Primary Examiner*—Nicky Chan
*Attorney, Agent, or Firm*—H. C. Young, Jr.

[57] ABSTRACT

Method of preparing tetraalkyl thiuram disulfides by racting a secondary amine with carbon disulfide in a substantially neutral solution of a saturated aliphatic alcohol and oxidizing the dithiocarbamate formed thereby with a hydroperoxide. The invention has particular utility by providing a relatively pollution-free method of preparing tetraalkyl thiuram disulfides.

1 Claim, No Drawings

METHOD OF PREPARING TETRAALKYL THIURAM DISULFIDES

This is a continuation of application Ser. No. 679,527 filed Apr. 23, 1976, now abandoned; which is a continuation of Ser. No. 493,577, filed Aug. 1, 1974, now abandoned, which was a continuation of application Ser. No. 301,692, filed Oct. 27, 1972, now abandoned.

This invention relates to an improved method of preparing tetraalkyl thiuram disulfides.

Tetraalkyl thiuram disulfides have typically been prepared in two stages. In the first step, one mole of secondary amine and one mole of base are reacted with one mole of carbon disulfide to give the dithiocarbamate, while in the second step, the salt, dithiocarbamate, is oxidized to the corresponding thiuram disulfide. A wide range of oxidizing agents have been proposed. Some consist of a combination of an oxidant with a strong mineral acid, such as sodium nitrite and sulfuric acid. A mole ratio of secondary amine to carbon disulfide of about 2:1 is typically required. The dithiocarbamate has also been oxidized with halogens or ammonium persulfate in neutral or alkaline mediums. In all of these cases, however, the inorganic byproducts formed during the reaction must be especially treated or be discharged as environmental pollutants. For example, neutralization of the effluent where sodium nitrite and sulfuric acid have been used produces the acid salt and amine byproducts as pollutants.

It is, therefore, an object of this invention to provide a relatively pollution-free process for the preparation of tetraalkyl thiuram disulfides.

In accordance with this invention, it has been discovered that a method of preparing tetraalkyl thiuram disulfides comprises reacting a secondary amine of the type $R_1R_2NH$ with carbon disulfide in a solution of a saturated aliphatic alcohol having 1 to 4 carbon atoms and oxidizing the dithiocarbamate formed thereby with a hydroperoxide selected from hydrogen peroxide, alkyl hydroperoxides and aralkyl hydroperoxides, where the said alcohol solution has a substantially autogeneous acid-base condition, and where $R_1$ and $R_2$ are individually selected from saturated alkyl radicals having 1 to 6 carbon atoms. It is preferred that the mole ratio of secondary amine to carbon disulfide is in the range of about 0.8:1 to about 1:1, although higher or lower ratios can be used with results of diminishing value.

A mole ratio of peroxide to dithiocarbamate of 0.5:1 is required by the stoichiometry of the reaction. A range of about 0.3:1 to about 0.7:1 is usually acceptable. A smaller ratio can result in insufficient oxidation and a larger ratio can result in over-oxidation.

Usually, a weight ratio of alcohol or alcohol-water mixture to secondary amine of about 30:1 to about 3:1, preferably about 20:1 to about 5:1, is used, depending on the desired thickness or viscosity of the mixture.

It is an important unexpected feature of this invention that the reaction of the peroxide with the dithiocarbamate, and without the aid of a strong mineral acid, efficiently produces with a good yield typically at least about 88 percent yield, a relatively high purity tetraalkyl thiuram disulfide of the formula:

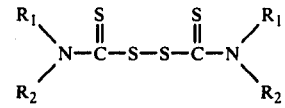

If desired, although not preferred, the starting alcohol solution can contain a certain amount of water without having a detrimental effect on the oxidation reaction. Thus, the starting alcohol solution can comprise about 100 to about 10, preferably about 100 to about 70, weight percent alcohol and, correspondingly, 0 up to about 90, preferably up to about 30, weight percent water based on the alcohol-water mixture.

It is a further important feature of this invention that the primary byproducts are water and alcohol, rather than the typical acid salts, thus, providing a substantially pollution-free process.

The unexpected features of this invention are amplified by an advantage of utilizing about an equal molar ratio of secondary amine to carbon disulfide to be in the range of about 0.8:1 to about 1:1, more preferably about 0.9:1 to about 1:1, and for the alcohol solution to be substantially neutral with its condition being the acidity or basicity autogenically developed by the reactants.

Thus, the combination of the substantially neutral alcohol solution without requiring the addition of a strong mineral acid, and the substantially equal molar ratio of secondary amine to carbon disulfide, particularly enhances the unexpected results.

Various alcohols can be used as the reaction medium of this invention, such as saturated aliphatic alcohols having 1 to 4 carbon atoms, representative of which are methyl alcohol, ethyl alcohol, isopropyl alcohol and t-butyl alcohol. Methyl alcohol and isopropyl alcohol are preferred.

Various secondary amines of the type $R_1R_2NH$, where $R_1$ and $R_2$ are preferably the same, can be used. Representative of the $R_1$ and $R_2$ radicals of the secondary amine are saturated aliphatic radicals having 1 to 5 carbon atoms such as methyl, ethyl, n-propyl, i-propyl, n-butyl, i-butyl, n-pentyl and i-pentyl radicals as well as phenyl radicals and other secondary amines of the type X=N—H, where X is tetramethylene, pentamethylene, hexamethylene group.

Representative of such secondary amines are dimethylamine, diethylamine, methylethylamine, di-n-propylamine, di-n-butylamine, diisopropylamine, di-n-pentylamine, diisopentylamine, N-methylaniline and various heterocyclic amines such as pyrrolidine, piperidine, morpholine and hexamethylene imine. The dimethylamine is preferred.

Various hydroperoxides can be used in the oxidation step of this invention. Representative of the various hydroperoxides are hydrogen peroxide, alkyl hydroperoxides and aralkyl hydroperoxides. The alkyl radicals of the hydroperoxides are saturated aliphatic radicals having 3 to 6 carbon atoms such as n-propyl, i-propyl, n-butyl, i-butyl, t-butyl, n-pentyl, i-pentyl, t-pentyl, n-hexyl, i-hexyl and t-hexyl radicals. Thus, representative of the alkyl hydroperoxides are t-butyl and t-amyl hydroperoxides and representative of the aralkyl hydroperoxides are cumene, ethyltoluene and ethylchlorobenzene hydroperoxides. Hydrogen peroxide is preferred.

In the further practice of this invention, a method is provided for producing valuable compounds as monomers which comprises dehydrating by conventional means the alcohols produced in the oxidation step of this invention. Thus, when cumene, ethyltoluene, ethylchlorobenzene and ethyl(t-butylbenzene) hydroperoxides are used, the corresponding alcohols obtained during the oxidation step of the dithiocarbamate can be dehydrated to the corresponding vinyl derivative. These products are valuable monomeric materials. For example, dimethylphenyl carbinol, methyltolyl carbinol, methylchlorophenyl carbinol and methyl(t-butylphenyl) carbinol can be obtained from cumene hydroperoxide, ethyltoluene hydroperoxide, ethylchlorobenzene hydroperoxide and ethyl(t-butylbenzene) hydroperoxide, respectively, which can, in turn, be dehydrated by conventional dehydration procedures to the corresponding compounds such as alpha methyl styrene, vinyltoluene, vinylchlorobenzene and vinyl(t-butylbenzene), respectively.

In this invention, the carbon disulfide and the secondary amine are typically reacted in the presence of the alcohol at a temperature in the range of about 0° C. to about 100° C., preferably about 30° C. to about 80° C., but not appreciably above the boiling point of the alcohol solution, at atmospheric pressure or above or below atmospheric pressure. The reaction can be conducted in batch or on a continuous basis.

The reaction of the secondary amine and carbon disulfide is very fast and the resulting dithiocarbamate is then substantially immediately oxidized with the hydroperoxide in the substantially neutral alcohol solution. Usually, a satisfactory temperature is in the range of about 0° C. to about 100° C., preferably about 30° C. to about 80° C., but not appreciably above the boiling point of the alcohol solution. The reaction can be conducted in bulk or on a continuous basis at atmospheric pressure or above or below atmospheric pressure. Usually the autogenous pressure of the mixture is satisfactory. The oxidation is typically fast and efficient without the addition of a strong mineral acid with essentially the only byproducts being water and alcohol.

The resulting tetraalkyl thiuram disulfide can then simply be recovered in high purity form by filtration or other suitable means.

As a result of the practice of this invention, various tetraalkyl thiuram disulfides can be prepared, representative of which are the tetramethyl, tetraethyl, tetrapropyl, tetraisopropyl, tetrabutyl, tetraisobutyl, tetrapentyl, tetraisopentyl, dimethyldiphenyl, ditetramethylene, dipentamethylene and dihexamethylene thiuram disulfides. Also, as a result of this practice, bis(morpholinothiocarbonyl) disulfide can be prepared.

The tetramethyl, tetraethyl and tetrabutyl are preferred with the preparation of tetramethyl thiuram disulfide from dimethyl amine being particularly enhanced by the method of this invention.

The practice of this invention is further illustrated by reference to the following examples which are intended to be representative rather than restrictive of the scope of the invention. Unless otherwise indicated, all parts and percentages are by weight.

EXAMPLE I

To a reactor fitted with a stirrer, reflux condenser, thermometer and addition funnel, was added 25 milliliters (ml), or 0.194 moles, of a 40 percent aqueous solution of dimethyl amine in 50 ml of isopropanol. The dimethyl amine solution was added dropwise over a five-minute period along with 16.4 grams (g), or 0.215 moles, of carbon disulfide. During this dropwise addition, the temperature of the mixture rose from about 28° C. up to about 45° C. The reaction mixture was then heated to a desired temperature and a solution consisting of 11 g of 30 percent aqueous hydrogen peroxide (0.097 moles) and 100 ml of isopropanol was added dropwise with stirring over a 15 minute period. The mixture was then cooled and the tetramethyl thiuram disulfide precipitate was filtered and allowed to dry.

Several such reactions were conducted at various temperatures and with the utilization of various isopropanol-water mixtures.

The results of experiments made utilizing various temperatures between about 40° C. and about 78° C. in 75 percent isopropanol are shown in Table 1 and identified as experiments 1-4.

Table 1

| Experiment | Temperature, ° C. | Yield, % | M.P., ° C. |
|---|---|---|---|
| 1 | 40-50° | 94 | 151-153 |
| 2 | 50° | 95 | 148-150 |
| 3 | 58-65° | 93 | 150-152 |
| 4* | 58-78° | 91 | 150-152 |

*Run performed at reflux temperature.

The results of the various experiments run utilizing various isopropanol-water solvent mixtures (before peroxide addition) are shown in Table 2 and identified as experiments 5-11.

Table 2

| Experiment | % Isopropanol | Temp., ° C. | Yield % | M.P., ° C. |
|---|---|---|---|---|
| 5 | 74.5 | 58-78° | 91 | 150-152 |
| 6 | 60.5 | 50-79° | 92 | 149-151 |
| 7 | 53.4 | 50-79° | 91 | 148-150 |
| 8 | 38.3 | 50-79° | 90 | 147-149 |
| 9 | 23.3 | 46-78° | 89 | 145-147 |
| 10 | 7.8 | 45-72° | 74 | 142-146 |
| 11 | 0 | 45-50° | 74 | 138-144 |

EXAMPLE II

Carbon disulfide was reacted with diethylamine in a solvent of isopropanol and various amounts of water according to the method of Example I. To the dithiocarbamate solution was then added, dropwise, 11.3 grams (g) of 30 percent aqueous hydrogen peroxide (0.1 moles hydrogen peroxide) dissolved in 100 ml of isopropanol with stirring over a 15 minute period at various temperatures. The resulting tetraethyl thiuram disulfide (TETD) was removed and the overall yield and its melting point determined. Several experiments were conducted utilizing this method to prepare the thiuram disulfide with solvents of various isopropanol/water ratios and at various temperatures and identified herein as experiments 12-20. The results of these experiments are more clearly shown in Table 3.

Table 3

| Experiment | Temp, ° C. | % Isopropanol | Yield | M P, ° C. |
|---|---|---|---|---|
| 12 | 30 | 100 | 90% | 66-67 |
| 13 | 55-70 | 100 | 85% | 68-69 |
| 14 | 30 | 80 | 85% | 66-67 |
| 15 | 50-70 | 80 | 88% | 67-68 |
| 16 | 30 | 60 | 84% | 65-67 |
| 17 | 50-70 | 60 | 92% | 63-65 |
| 18 | 30 | 40 | 84% | 62-65 |
| 19 | 50-65 | 40 | 92% | 65-66 |
| 20 | 45-80 | 100% water | 80% | 60-63 |

As shown in Table 3, when the reaction and oxidation are conducted with the peroxide in the presence of the alcohol, particularly at a reduction in temperature, both the yield and melting point of the tetraethyl thiuram disulfide are substantially enhanced.

EXAMPLE III

Carbon disulfide was reacted with di-n-propyl amine in the presence of a solvent of isopropanol and water or water according to the method of Example I. To the resulting dithiocarbamate solution was then added aqueous hydrogen peroxide dissolved in isopropanol according to the method of Example II and the resulting tetrapropyl thiuram disulfide (TPTD) was removed and its yield and melting point determined.

Two experiments were run utilizing the method of this example and identified herein as experiments 21 and 22. In experiment 21, the reaction was conducted at 30° C. with the solvent being 80 weight percent isopropanol and experiment 22 was conducted using a temperature in the range of about 55° C. to 70° C. with the solvent being water. As shown in the following Table 4, both the yield and melting point of the tetrapropyl thiuram disulfide were substantially increased with the use of the alcohol.

Table 4

| Experiment | Temp. ° C. | Solvent | Yield | M P, ° C. |
|---|---|---|---|---|
| 21 | 30 | 80% isopropanol | 92.5% | 47.5–48.5 |
| 22 | 55–70 | water | 79% | 45–46 |

EXAMPLE IV

Carbon disulfide was reacted with pentamethylene imine in a solvent of isopropanol and water or water according to the method of Example I. The resulting dithiocarbamate solution was then oxidized with hydrogen peroxide according to the method of Example 2. In this example, three experiments were run at various temperatures and identified herein as experiments 23–25. As shown in Table 5, both the yield and melting point were substantially increased with the use of the alcohol, as compared to water as a solvent and even further increased as the temperature of the reaction was somewhat lowered.

Table 5

| Experiment | Temp, ° C. | Solvent | Yield | M P, ° C. |
|---|---|---|---|---|
| 23 | 45–70° | 80% isopropanol | 90% | 120–122 |
| 24 | 41–43° | 80% isopropanol | 93% | 124–125 |
| 25 | 45–70° | water | 69% | 107–113 |

While certain representative embodiments and details have been shown for the purpose of illustrating the invention, it will be apparent to those skilled in this art that various changes and modifications may be made therein without departing from the spirit or scope of the invention.

What is claimed is:

1. A method of preparing tetramethyl thiuram disulfide which consists essentially of (A) reacting dimethylamine with carbon disulfide at a temperature in the range of about 30° C. to about 80° C. in a solution of a solvent of 10–100 weight percent alcohol selected from at least one of methyl alcohol, ethyl alcohol, isopropyl alcohol or t-butyl alcohol, and correspondingly, 90–0 weight percent water, then (B) oxidizing the dithiocarbamate formed by the dimethylamine/carbon disulfide reaction at a temperature in the range of about 0° C. to about 100° C., but not appreciably above the boiling point of the alcohol, substantially immediately after the addition of said dimethylamine, by the addition of hydrogen peroxide while (C) maintaining the acid-base condition of said solution only as the condition generated by the reactants and products themselves; where the mole ratio of the dimethylamine to carbon disulfide is in the range of about 0.8/1 to aboout 1/1 and where the mole ratio of peroxide to dithiocarbamate is in the range of about 0.3/1 to about 0.7/1.

* * * * *